(12) United States Patent
Hofmann et al.

(10) Patent No.: US 7,973,934 B2
(45) Date of Patent: Jul. 5, 2011

(54) PLASMON RESONANCE SENSOR

(75) Inventors: Andreas Hofmann, Wallenfels (DE);
Norbert Danz, Jena (DE)

(73) Assignees: Andreas Hofmann, Wallenfels (DE);
Fraunhofer-Gesellschaft zur Foerderung Angewandter Forschung E.V., Munich (DE)

( * ) Notice: Subject to any disclaimer, the term of this patent is extended or adjusted under 35 U.S.C. 154(b) by 152 days.

(21) Appl. No.: 12/438,911

(22) PCT Filed: Aug. 24, 2007

(86) PCT No.: PCT/EP2007/007442
§ 371 (c)(1),
(2), (4) Date: Feb. 25, 2009

(87) PCT Pub. No.: WO2008/025488
PCT Pub. Date: Mar. 6, 2008

(65) Prior Publication Data
US 2009/0262357 A1 Oct. 22, 2009

(30) Foreign Application Priority Data
Sep. 1, 2006 (DE) .......................... 10 2006 041 338

(51) Int. Cl.
*G01N 21/55* (2006.01)
(52) U.S. Cl. ........................................ 356/445; 356/448

(58) Field of Classification Search ........... 356/445–448
See application file for complete search history.

(56) References Cited

U.S. PATENT DOCUMENTS

| 5,917,607 | A | * | 6/1999 | Naya | 356/445 |
| 6,801,317 | B2 | | 10/2004 | Hofmann | |

FOREIGN PATENT DOCUMENTS

| DE | 100 23 363 | 12/2001 |
| DE | 100 55 655 | 5/2002 |
| DE | 103 24 973 | 12/2004 |
| EP | 0 305 109 | 3/1989 |
| WO | 01/862 62 | 11/2001 |
| WO | 02/39095 | 5/2002 |
| WO | 2004/061434 | 7/2004 |
| WO | 2004/106901 | 12/2004 |

* cited by examiner

*Primary Examiner* — Michael P Stafira
(74) *Attorney, Agent, or Firm* — Michael J. Striker

(57) ABSTRACT

The plasmon resonance sensor (1) comprises a chip (2) of transparent plastic with a gold layer (3) made up of narrow part surfaces (4), arranged in a row, on the inner side of which light from a planar light source (12) is convergently guided. A Fourier lens (24) integrated in the chip (2) forms the reflected angular spectrum on the detector (23), arranged at a focal separation (F) from the integrated Fourier lens (24) for temporal determination of the incident angle with a resonant intensity minimum of reflected light. An incident lens (13) brings about imaging of the planar light source (12) in the form of lines of light on the part surfaces (4), which are further imaged in the form of lines of light on the detector (23).

16 Claims, 3 Drawing Sheets

Fig. 3
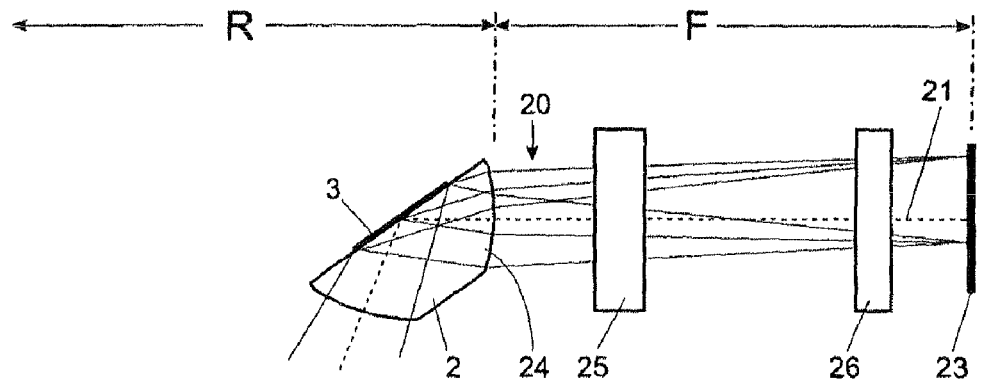
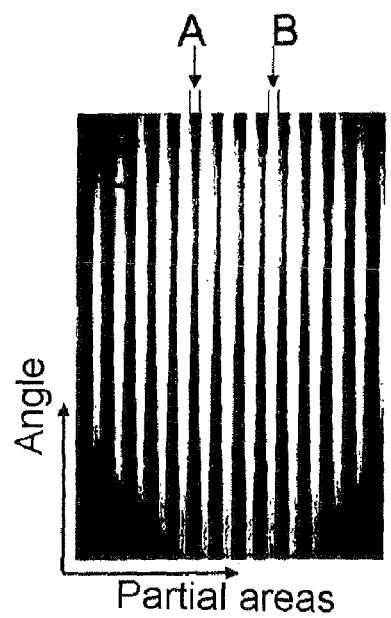
Fig. 4
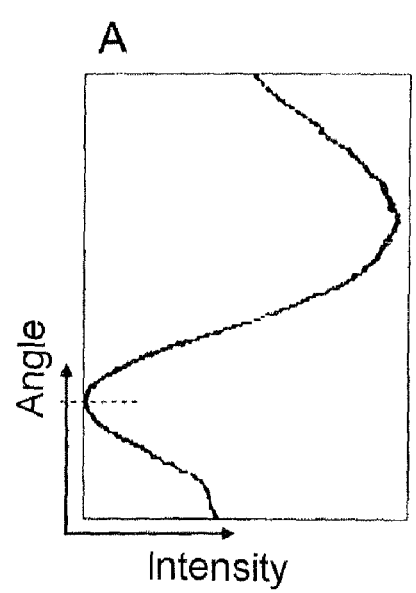
Fig. 5

PLASMON RESONANCE SENSOR

CROSS-REFERENCE TO RELATED APPLICATION

The invention described and claimed hereinbelow is also described in German Patent Application DE 10 2006 041 338.5 filed on Sep. 1, 2006. This German Patent Application, whose subject matter is incorporated here by reference, provides the basis for a claim of priority of invention under 35 U.S.C. 119(a)-(d).

BACKGROUND OF THE INVENTION

The invention relates to a plasmon resonance sensor, in particular for biosensor technology, comprising a light-transmissive body, a—applied to an area of the body—reflective metal layer or semiconductor layer having a surface which can be sensitized to molecules to be detected, which comprises partial areas arranged alongside one another in a series and serving for forming a respective one of a plurality of measurement cells, comprising an areal light source for producing a beam path incident on the inner side of the layer through the body, and comprising a detector, which captures the reflected emergent beam path and ascertains in a time-dependent manner the angle of incidence of the light which changes as a result of molecular attachments to the sensitive surface and in the case of which an intensity minimum of emergent light occurs owing to resonance, a Fourier lens being arranged in the emergent beam path and the detector being arranged at the focal point distance with respect to the Fourier lens.

The phenomenon of surface plasmon resonance (SPR) involves a collective excitation of the electrons at the surface of a layer having free electrons. The resonant frequency of the surface plasmons is highly sensitive to the refractive index of the medium adjacent to the sensitive surface. This can be used to measure thin layers with regard to the refractive index or the layer thickness (up to approximately one light wavelength). In biosensor technology, in particular, this effect is used to examine the kinetics of attachment of biomolecules from a sample liquid to a functionalized metal surface. For this purpose, the resonance condition of the surface plasmons is detected in time-resolved fashion. The surface plasmons of the thin metal layer are excited by light that falls onto the metal layer at a specific angle or angular range. The resonance condition is then met for a specific combination of wavelength and angle of incidence. Under this resonance condition, the intensity of the light reflected at the metal layer is significantly reduced on account of the generation of surface plasmons. In order to find the resonance condition, either the angle of incidence (given a constant wavelength) or the wavelength (given a constant angle of incidence) can be tuned and the intensity of the reflected light can be detected. A gold-coated glass body (prism) and light having a constant wavelength, which impinges on the gold layer at different angles of incidence, are generally employed.

It is known from EP 305 109 B1 in the case of angle-resolved measurement, to produce the corresponding angular range optically by means of a beam fan which is focused onto the metal layer by means of a hemispherical glass lens. The focusing enables only a single measurement, after which the layer which is sensitive to molecules has to be regenerated again before a further measurement becomes possible. Moreover, owing to the focusing, there is the risk of local heating of the metal layer and, as a result of this, the possibility of corruption of the measurement values.

DE 100 23 363 C1 has already disclosed realizing different angles of incidence of the light by irradiating the metal layer with a divergent light beam which issues from a point light source in the form of a laser diode. In this case, simultaneous multiple measurements of different samples are made possible by virtue of the fact that the incident light is fed divergently only in one direction (in the incidence plane), while it is collimated by means of a cylindrical lens in the direction perpendicular thereto, a plurality of measurement cells being arranged in a series transversely with respect to the incidence plane on the metal layer. Harmful heating of the metal layer is prevented owing to the divergent irradiation. Within the incidence plane or divergence plane, different angles of incidence are present in each case at a different location of the metal layer. This leads to an influencing of the measurement values owing to inhomogeneities of the metal layer. Furthermore, the still divergently emergent beam path is detected directly, which necessitates large detectors that are each assigned to a single measurement cell. This leads to a complicated and spatially extended device which enables only a small number of measurement cells and thereby simultaneous measurements.

DE 100 55 655 C2 discloses the plasmon resonance sensor comprising a plurality of measurement cells as described in the introduction. In this case, each measurement cell or partial area of the metal layer is assigned a dedicated light source formed by an optical waveguide having an extended and not point-type emission area, the optical waveguides being directly connected to the light-transmissive body and a Fourier lens and a cylindrical lens being arranged in the emergent beam path, which permits a common detector. The areal light sources, which are in each case comparable to a multiplicity of adjacent point light sources, have the consequence that the range of different angles of incidence is present at all locations of the metal layer. The Fourier lens is arranged for the purposes of a Fourier imaging of a 2 f arrangement between the emission areas of the light sources and the detector, the emergence optical unit ensuring that identical angles of incidence are combined on the detector and are separated therefrom light based on other angles of incidence. It is thus possible to obtain exact averaged measurement results which are free from unfavorable influences due to heating or inhomogeneities of the metal layer.

What is disadvantageous about this known plasmon resonance sensor, however, is that each measurement cell or partial area of the metal layer is assigned a dedicated areal light source, which greatly limits the possible number of measurement cells. Moreover it is not easy to obtain an angular spectrum which encompasses the entire angular range to be measured and which is dependent on the distance between the optical fiber and the metal surface, the numerical aperture of the fiber and the fiber diameter. In addition, the divergent emission of the metal layer requires a comparatively extended optical unit with a large Fourier lens which captures the emergent beam path. That, too, is detrimental to a compact and uncomplicated design.

SUMMARY OF THE INVENTION

Accordingly, the invention is based on the object of improving this plasmon resonance sensor such that, whilst maintaining the advantages outlined, it is simpler and more compact and has greater performance.

Proceeding from the sensor described in the introduction, this object is achieved according to the invention by virtue of the fact that an incidence optical unit is provided between the light source and the layer, and it collimates the incident beam path in the series direction of the partial areas and directs it onto the layer convergently in the incidence plane running perpendicular to the series direction of the partial areas, such that the single areal light source is imaged on each partial area of the layer in the form of a luminous line.

The convergent irradiation of the metal layer enables a compact design with small components or optical elements both on the light incidence side and on the light emergence side, in which case very narrow partial areas which are closely adjacent to one another can also be employed in the interests of a large number of measurement cells.

Expedient configurations and developments of the invention are apparent from the dependent claims. In this case, in particular the use of a chip composed of a light-transmissive polymeric plastic as light-transmissive body contributes to simplification and increase in performance since it can be produced inexpensively and simultaneously by corresponding shaping also with optical functions for the light guiding on the emergence side, and if appropriate also on the incidence side, by way of injection molding, as is known in principle from DE 103 24 973 B4. This affords the possibility of designing the chip as a replaceable disposable article, such that regeneration measures become superfluous and not only can a plurality of measurements be carried out simultaneously but the multiple measurements can also be performed in rapid succession. A comparatively expensive optical component is obviated as a result of the integration of the collimation lens into the chip. Furthermore, the insertion of the chip into the plasmon resonance sensor results in an optical coupling between the illumination optics and the detection optics without a disturbance-prone coupling by means of immersion media.

BRIEF DESCRIPTION OF THE DRAWINGS

An exemplary embodiment of the invention is explained in more detail below with reference to a schematic drawing, in which:

FIG. 3 shows the right-hand part according to FIG. 1 in a somewhat enlarged and overall pivoted illustration;

FIG. 4 shows an image of the irradiated partial areas that is produced on the detector;

FIG. 5 shows the measured angle-dependent intensity distribution along a partial area;

DESCRIPTION OF THE PREFERRED EMBODIMENTS

Figure 1:
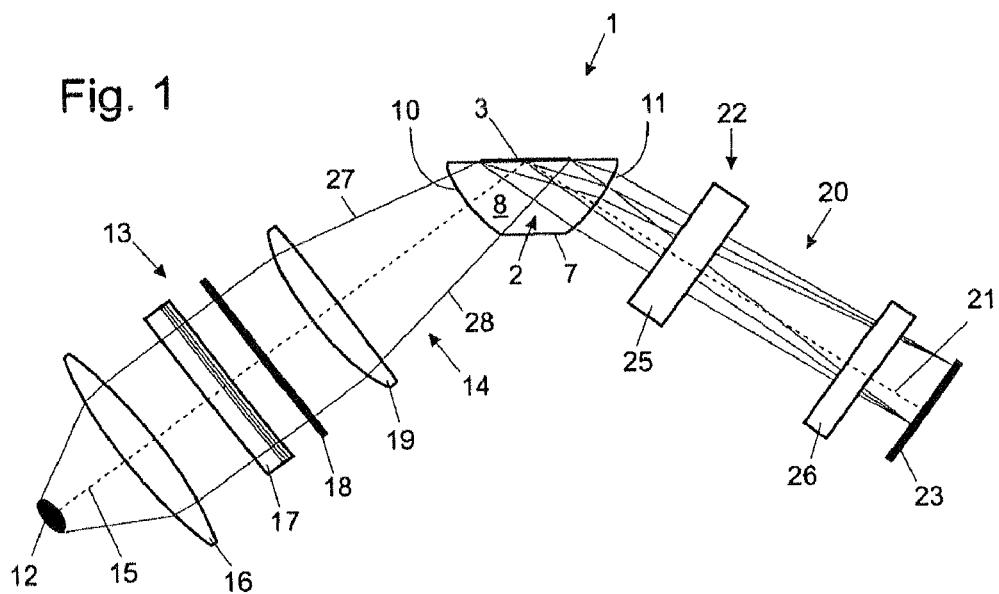
FIG. 1 shows the parts of the plasmon resonance sensor which are essential for the invention, in a side view.
Figure 2:
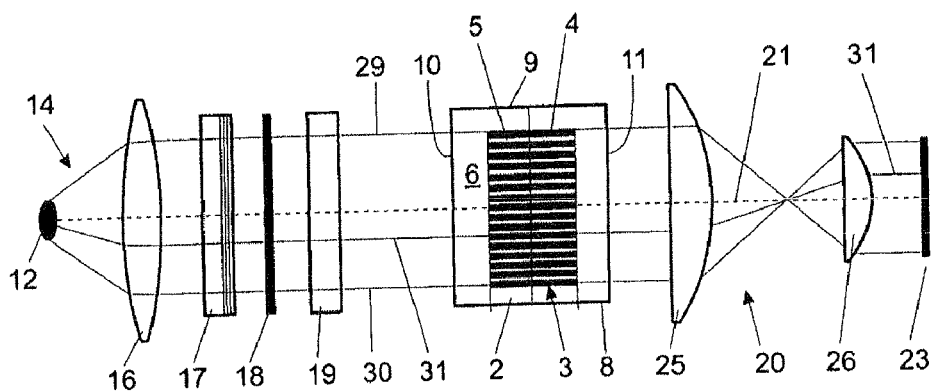
FIG. 2 shows the arrangement according to FIG. 1 in plan view, but with light incidence and light emergence sides pivoted up in coaxial alignment and adapted to the side view width.

The plasmon resonance sensor 1, the essential parts of which are illustrated in FIGS. 1 and 2, has a light-transmissive body 2, which is a chip composed of a polymeric plastic and produced by injection molding. This chip 2 bears on its top side 6 a light-reflecting thin metal layer 3, which is preferably composed of gold. By means of a chemical modification of the gold surface, the latter acquires a structure wherein individual narrow partial areas 4 which are arranged closely adjacent to one another and are spaced apart by intermediate strips 5 are arranged alongside one another in a series (FIG. 2). The chip 2 has a planar top side 6 and a planar underside 7 parallel thereto, which are connected to one another by likewise planar end sides 8 and 9. By contrast, the side faces 10 and 11, as can be seen from FIGS. 1 and 3, are cylindrically curved.

The chip 2 is assigned a light source 12 and an incidence optical unit 13, whereby an incident beam path 14 with optical incidence axis 15 is produced, said beam path penetrating into the chip 2 through the side face 10 and being incident on the inner side of the reflective metal layer 3.

The light source 12, as indicated in the illustration, is an areal or extended light source, the emission area of which comprises as it were a multiplicity of adjacent point light sources which each emit within a specific angular range. By way of example, the end face of a so-called multimode fiber or LED is used as such a light source.

The incidence optical unit 13 comprises, as viewed in the direction of incidence, a spherical lens 16, which firstly collimates the incident beam path 14, that is to say parallelizes the light beams, and also a wavelength filter 17, a polarization filter 18 and a cylindrical lens 19, which converts the incident beam path 14 into a beam bundle that is convergent in the incidence plane (FIG. 1), but in the direction perpendicular thereto, that is to say in the series direction of the partial areas 4, leaves it in the parallel orientation (FIG. 2). With the curved side face 10 of the chip 2 it is also possible, if appropriate, for a part of the incidence optical unit 13 to be integrated into the chip 2. The incidence optical unit 13 described has the effect that the light source is imaged in the direction of the incidence plane on the partial areas 4, while in the direction perpendicular to the incidence plane the partial areas arranged alongside one another are illuminated in identical fashion (in collimated fashion).

The reflection of the incident beam path 14 at the metal layer 3 or the partial areas 4 thereof gives rise to an emergent beam path 20 with the optical emergence axis 21, which beam path emerges through the side face 11 of the chip 2 and is directed onto a detector 23 by means of an emergence optical unit 22. The detector 23 can be a CCD sensor (CCD chip) in the manner of a 2D camera and continuously measures, separately for each partial area 4, the angle-of-incidence-specific intensity of the reflected light.

The emergence optical unit 22 includes a cylindrical Fourier lens 24, which is formed by the cylindrically curved side face 11 of the chip 2 and is therefore integrated into the chip, and also a larger cylindrical lens 25 and a smaller cylindrical lens 26, which bring about an imaging of the partial areas 4 or of the luminous lines present thereon on the detector 23.

FIG. 3 makes it clear that the radius R of curvature of the side face 11 or of the integrated Fourier lens 24 distinctly exceeds the distance thereof from the partial areas 4. By way of example, given a distance of 5 mm from the gold layer 3, the radius R of curvature is 28 mm, that is to say five to six times the distance. The detector 23 is arranged at the focal distance F with respect to the integrated Fourier lens 24, such that a so-called "Fourier imaging" arises on it and, for each illuminated partial area 4, the rays incident thereon at the same angle in distributed fashion are combined at a point on the detector 23, as is illustrated for two points in FIGS. 1 and 3.

Although the 2 f arrangement, which is traditional for a Fourier imaging and in which the object to be imaged is also arranged at the focal point distance with respect to the lens, cannot be realized with the integrated lens 24, a separate Fourier lens would have to be of a considerable size and would be correspondingly voluminous, heavy and expensive. The radius R of curvature of the integrated Fourier lens 24 thus determines the distance from the detector 23 at which the image of the angular spectrum arises (image distance), and also the size of the image. The cylindrical lenses 25 and 26 provided in the emergent beam path counteract blurring of the imaging of the partial areas 4 on the detector 23. Such blurring results from the area extent of the light source 12 and a divergence of the emergent light bundle in the series direction and also from diffraction effects at the edges of the partial areas 4.

In order to illustrate the optical conditions of the plasmon resonance sensor 1, FIGS. 1 to 3 depict the course of a plurality of rays from the light source 12 as far as the detector 23, to be precise—from the standpoint of the incidence side—the upper limiting ray 27, the lower limiting ray 28, the left-hand limiting ray 29 and the right-hand limiting ray 30 and also a central ray 31. It should be noted in this respect that the corresponding ray angles are present over the entire light beam cross section owing to the special light source 12 having an areal emission area within the incident beam path 14 and also the chip 2. FIGS. 1 and 3 show the ray refraction—which only occurs in the incidence plane—by the Fourier lens 24, integrated into the chip 2, with a non-telecentric—that is to say not parallel to the optical emergence axis 21—concentration of the rays having an identical angle of incidence.

FIG. 4 shows the intensity distribution on the detector 23. The dark stripes A and the bright stripes B arise as a result of the fact that the layer 3 on the chip 2 was wetted with water. In the uncoated intermediate strips 5, the light coming from the light source 12 is completely reflected (total reflection), whereby the bright stripes B arise. In the regions formed by the metal-coated partial areas 4, by contrast, the plasmon resonance effect is observed, which is reproduced by the dark stripes A.

The intensity distribution along such a stripe A that is measured at a specific point in time can be seen from FIG. 5. In this case, the dashed line highlights the position of the intensity minimum corresponding to a specific angle of incidence. This minimum position, which shifts in a time-dependent manner with increasing attachment of molecules, is determined precisely.

Figure 6:
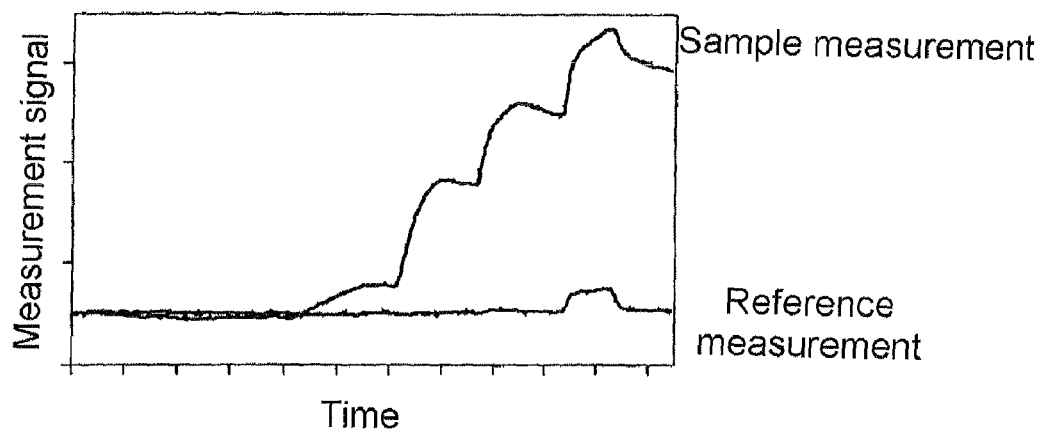
FIG. 6 shows the temporal development of the position of the minimum of the resonance for a sample measurement and a reference measurement.

FIG. 6 shows the temporal development of the position of the minimum of the resonance for two different partial areas 4 on the chip. One partial area, a reference partial area, essentially only comprises the gold coating, while the other partial area, a sample partial area, was immobilized with protein A. In the experiment, antibody solutions and water were alternately directed over the partial areas 4, and the concentration of the antibody solution was increased from step to step. The specific binding of the antibodies to the sample partial area leads to the observed association (wetting with antibody solution) or disassociation (wetting with water) of the antibodies at the binding surface. A signal is observed at the reference partial area only in the region of high antibody concentration, said signal being attributable to the increased refractive index of this solution.

Figure 7:
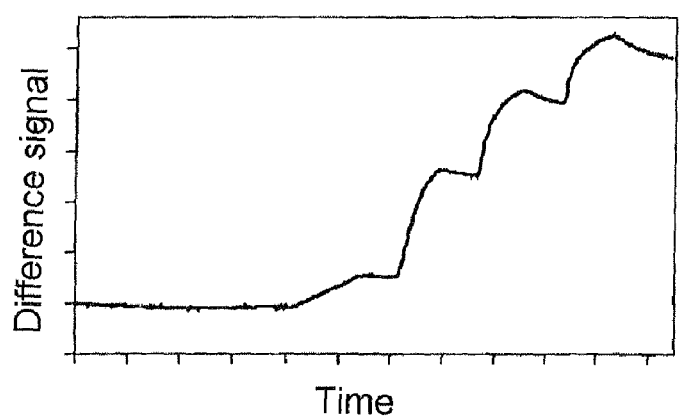
FIG. 7 shows the time-dependent profile of the difference signal obtained from the two curves according to FIG. 6.

The measurements in accordance with FIG. 6 were carried out simultaneously and for relatively inhomogeneous illumination with an intensity distribution superposing the resonance curves. FIG. 7 shows the profile of the difference signal that results from the two curves in FIG. 6. The irregular form of the binding curve at the highest antibody concentration is corrected in this case. In addition, noise that affects both partial areas 4 equally can be reduced by the difference formation. A further advantage of the reference measurement is that the influence of non-specific bindings can be corrected.

In accordance with the simultaneous measurement of sample values and assigned reference value, the partial areas 4 are divided into measurement areas for the samples and into at least one reference area. Each measurement area can also be assigned a dedicated reference area.

The formation of the partial areas can be obtained by a corresponding structuring of the layer 3 or else by a chemical modification of the surface thereof. In this case, it may be advantageous firstly to form partial areas of identical type and then to subdivide them into measurement areas and into reference areas by means of a chemical surface modification.

The invention claimed is:

1. A plasmon resonance sensor, in particular for biosensor technology, comprising a light-transmissive body (2), a—applied to an area of the body (2)—reflective metal layer (3) or semiconductor layer having a surface which can be sensitized to molecules to be detected, which comprises partial areas (4) arranged alongside one another in a series and serving for forming a respective one of a plurality of measurement cells, comprising an areal light source (12) for producing a beam path (14) incident on the inner side of the layer (3) through the body (2), and comprising a detector (23), which captures the reflected emergent beam path (20) and ascertains in a time-dependent manner the angle of incidence of the light which changes as a result of molecular attachments to the sensitive surface and in the case of which an intensity minimum of emergent light occurs owing to resonance, a Fourier lens (24) being arranged in the emergent beam path (20) and the detector (23) being arranged at the focal point distance (F) with respect to the Fourier lens (24), wherein an incidence optical unit (11) is provided between the light source (12) and the layer (3), and it collimates the incident beam path (14) in the series direction of the partial areas (4) and directs it onto the layer (3) convergently in the incidence plane running perpendicular to the series direction of the partial areas (4), such that the light source (12) is imaged on each partial area (4) of the layer (3) in the form of a luminous line, and wherein a common light source is assigned to the partial areas (4) and provides contemporaneous beaming of all of the partial areas (4).

2. The plasmon resonance sensor as claimed in claim 1, wherein the layer (3) is structured to form partial areas (4).

3. The plasmon resonance sensor as claimed in claim 1, wherein the partial area structure is obtained wholly or partly by a chemical modification of the surface of the layer (3).

4. The plasmon resonance sensor as claimed claim 1, wherein provision is made of a partial area structure having strip- or line-shaped partial areas (4) which are spaced apart by intermediate strips (5).

5. The plasmon resonance sensor as claimed in claim 1, wherein the partial areas (4) are divided into measurement areas and at least one reference area.

6. The plasmon resonance sensor as claimed in claim 5, wherein each measurement area is assigned a dedicated reference area.

7. The plasmon resonance sensor as claimed in claim 3, wherein the reference areas are obtained by a subsequent structuring by way of chemical surface modification.

8. The plasmon resonance sensor as claimed in claim 1, wherein the light-transmissive body is a chip (2) composed of a polymeric plastic.

9. The plasmon resonance sensor as claimed in claim 8, wherein the chip (2) is produced by injection molding.

10. The plasmon resonance sensor as claimed in claim 1, wherein the Fourier lens (24) assigned to the emergent beam path (20) is integrated into the light-transmissive body (2).

11. The plasmon resonance sensor as claimed in claim 10, wherein the radius (R) of curvature of the integrated Fourier lens (24) exceeds the distance thereof from the layer (3) by at least 1.5 fold.

12. The plasmon resonance sensor as claimed in claim 1, wherein the incidence optical unit (13) is at least partly integrated into the light-transmissive body (2).

13. The plasmon resonance sensor as claimed in claim 1, wherein the incidence optical unit (13) has a collimation lens (16) for collimating the incident beam path (14) and a downstream cylindrical lens (19) for obtaining the convergence in the incidence plane whilst maintaining the collimation perpendicular to the incidence plane.

14. The plasmon resonance sensor as claimed in claim 13, wherein a wavelength filter (17) and a polarization filter (18) are arranged between the collimation lens (16) and the cylindrical lens (19).

15. The plasmon resonance sensors claimed in claim 1, wherein the common light source (12) is a light emitting diode.

16. A plasmon resonance sensor, in particular for biosensor technology, comprising a light-transmissive body (2), a—applied to an area of the body (2)—reflective metal layer (3) or semiconductor layer having a surface which can be sensitized to molecules to be detected, which comprises partial areas (4) arranged alongside one another in a series and serving for forming a respective one of a plurality of measurement cells, comprising an areal light source (12) for producing a beam path (14) incident on the inner side of the layer (3) through the body (2), and comprising a detector (23), which captures the reflected emergent beam path (20) and ascertains in a time-dependent manner the angle of incidence of the light which changes as a result of molecular attachments to the sensitive surface and in the case of which an intensity minimum of emergent light occurs owing to resonance, a Fourier lens (24) being arranged in the emergent beam path (20) and the detector (23) being arranged at the focal point distance (F) with respect to the Fourier lens (24), wherein an incidence optical unit (11) is provided between the light source (12) and the layer (3), and it collimates the incident beam path (14) in the series direction of the partial areas (4) and directs it onto the layer (3) convergently in the incidence plane running perpendicular to the series direction of the partial areas (4), such that the light source (12) is imaged on each partial area (4) of the layer (3) in the form of a luminous line, and wherein a common light source is assigned to the partial areas (4) and provides contemporaneous beaming of all of the partial areas (4); wherein the chip (2) is produced by injection molding, wherein the Fourier lens (24) assigned to the emergent beam path (20) is integrated into the light-transmissive body (2), and wherein the incidence optical unit (13) is at least party integrated into the light-transmissive body (2).

* * * * *